US00PP27780P2

(12) United States Plant Patent
Sidhu

(10) Patent No.: US PP27,780 P2
(45) Date of Patent: Mar. 14, 2017

(54) ***RHODODENDRON* PLANT NAMED 'PJM ELITE STAR'**

(50) Latin Name: ***Rhododendron minus*×*Rhododendron dauricum***
Varietal Denomination: PJM Elite Star

(71) Applicant: Gurjit Sidhu, Mission (CA)

(72) Inventor: Gurjit Sidhu, Mission (CA)

( * ) Notice: Subject to any disclaimer, the term of this patent is extended or adjusted under 35 U.S.C. 154(b) by 103 days.

(21) Appl. No.: 14/544,895

(22) Filed: Mar. 4, 2015

(51) Int. Cl.
*A01H 5/02* (2006.01)

(52) U.S. Cl.
USPC ..... Plt./238

(58) Field of Classification Search
USPC ..... Plt./238
See application file for complete search history.

*Primary Examiner* — Keith Robinson
(74) *Attorney, Agent, or Firm* — Penny J. Aguirre

(57) ABSTRACT

A new cultivar of hybrid *Rhododendron* plant named 'PJM Elite Star' that is characterized by its flowers that are deep purple-violet-red in color, its early spring blooming habit, its densely branched plant habit, and its summer foliage that is dark green in color and winter foliage that is dark reddish brown in color.

2 Drawing Sheets

Botanical classification: *Rhododendron minus*×*Rhododendron dauricum.*

Cultivar designation: 'PJM Elite Star'.

BACKGROUND OF THE INVENTION

The present invention relates to a new and distinct cultivar of *Rhododendron* plant of hybrid origin, botanically known as *Rhododendron* 'PJM Elite Star' and will be referred to hereafter by its cultivar name, 'PJM Elite Star'. 'PJM Elite Star' is a new cultivar of deciduous *Rhododendron* grown for use as a landscape plant.

The inventor discovered the new cultivar, 'PJM Elite Star', growing in a container block of *Rhododendron* 'PJM Elite' (not patented) at his nursery in Mission, British Columbia, Canada in spring of 2012. The plants of 'PJM Elite' derived from cuttings and it is therefore presumed that 'PJM Elite Star' arose as a branch mutation of 'PJM Elite'.

Asexual propagation of the new cultivar was first accomplished by in vitro propagation under the direction of the Inventor in Mission, British Columbia in April of 2012. Asexual propagation by in vitro propagation and stem cuttings has determined that the characteristics of the new cultivar are stable and are reproduced true to type in successive generations.

SUMMARY OF THE INVENTION

The following traits have been repeatedly observed and represent the characteristics 'PJM Elite Star'. These attributes in combination distinguish 'PJM Elite Star' as a new and distinct cultivar of *Rhododendron.*

1. 'PJM Elite Star' exhibits flowers that are deep purple-violet-red in color.
2. 'PJM Elite Star' exhibits an early spring blooming habit in Mission, British Columbia, but commences bloom one week later than its parent plant.
3. 'PJM Elite Star' exhibits an upright, densely branched plant habit.

4. 'PJM Elite Star' exhibits summer foliage that is dark green in color and winter foliage that is dark reddish brown in color.

The female parent of 'PJM Elite Star', 'PJM Elite', differs from 'PJM Elite Star' in having flowers that are lighter purple-violet that lack red tones in color and in commencing bloom one week earlier. 'PJM Elite Star' can be most closely compared to the *Rhododendron* cultivars 'PJM' (not patented) and 'PJM Pink Delight' (U.S. Plant Pat. No. 18,328). 'PJM' differs from 'PJM Elite Star' in having flowers that are purple-blue/lavender in color. 'PJM Pink Delight' differs from 'PJM Elite Star' in having flowers that are light lavender pink in color.

BRIEF DESCRIPTION OF THE DRAWINGS

The accompanying colored photographs illustrate the overall appearance and distinct characteristics of the new *Rhododendron*. The photographs were taken of plants 3 years in age as grown in a one-gallon nursery container in a greenhouse in Mission, British Columbia.

The photograph in FIG. 1 provides a view of the overall plant habit of 'PJM Elite Star' in bloom.

Figure 1:
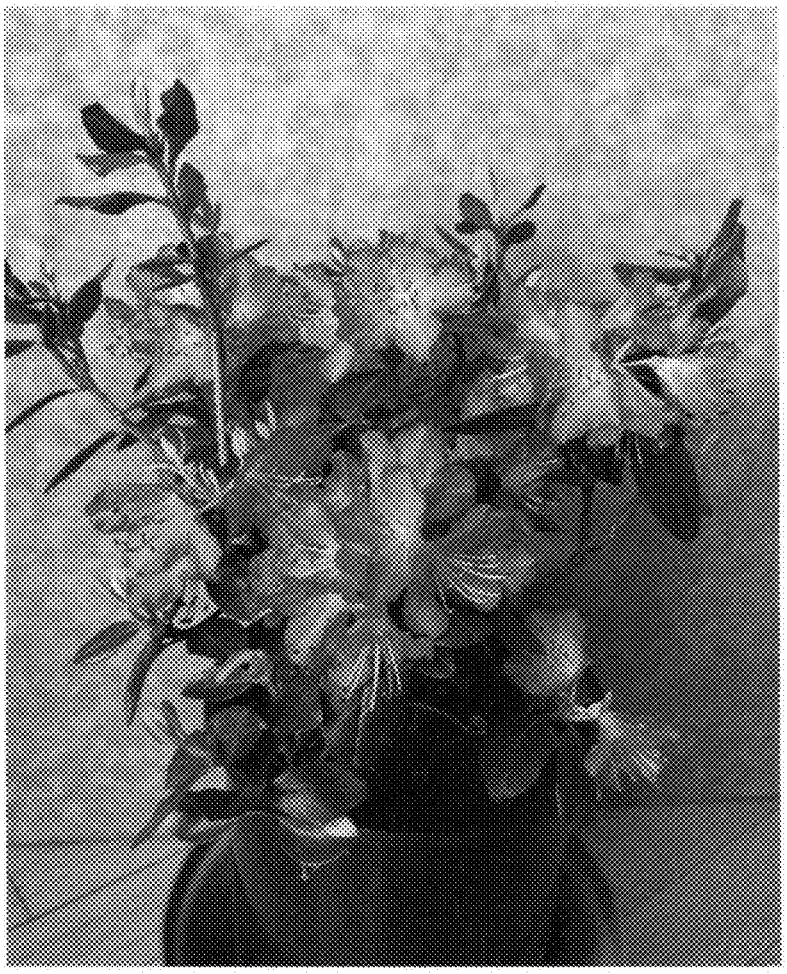
Figure 2:
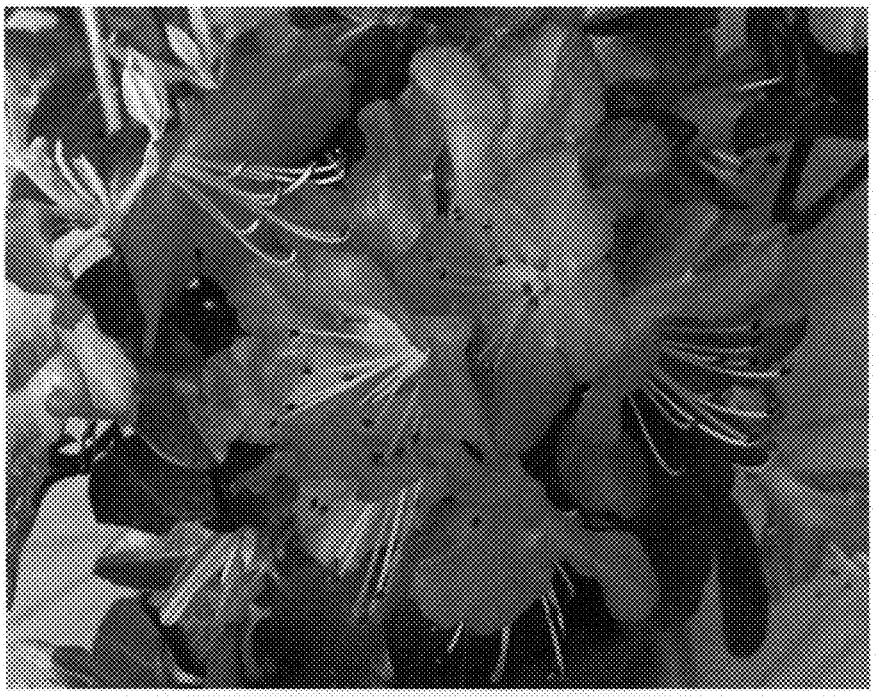

The photograph in FIG. 2 provides a close-up view of an inflorescence of 'PJM Elite Star'.

Figure 3:
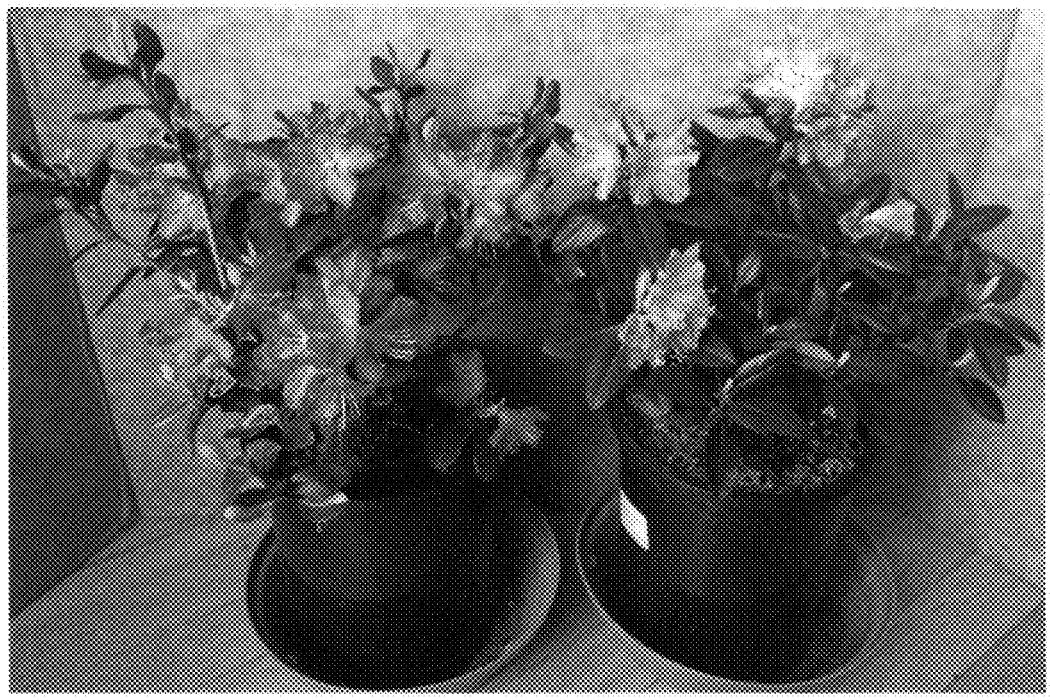

The photograph in FIG. 3 provides a comparison between a plant of 'PJM Elite Star' (left) and 'PJM Elite' (left).

The colors in the photographs are as close as possible with the digital photography techniques available, the color values cited in the detailed botanical description accurately describe the colors of the new *Rhododendron.*

DETAILED BOTANICAL DESCRIPTION OF THE PLANT

The following is a detailed description of plants 3 years in age as grown in one-gallon nursery containers in a greenhouse in Mission, British Columbia. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General characteristics:

*Blooming period*.—Early spring in British Columbia.

*Plant type*.—Evergreen shrub.

*Plant habit*.—Upright and densely branched.

*Height and spread*.—An average of 30 cm in height and width as a three year-old plant grown in a one-gallon container, mature size in the landscape has yet to be determined.

*Cold hardiness*.—At least to U.S.D.A. Zone 4.

*Diseases and pests*.—No susceptibility and resistance to diseases or pests has been observed.

*Root description*.—Shallow and very finely fibrous.

*Propagation*.—In vitro propagation (preferred) or softwood stem cuttings.

*Time required for root initiation*.—3 to 4 weeks after TC plantlets are placed in 288 plug tray containing rooting media composed of peat and perlite.

*Time required for root development*.—Rooted plantlets in 288 plug trays produce sufficient roots for transplanting into 2 inch pot in approximately 12 weeks after being placed in the plug tray.

*Growth rate*.—Moderate.

Stem description:

*Shape*.—Round-oval.

*Stem color*.—New growth; 144B, mature wood; a blend of N199B, N199C, and N199D.

*Stem size*.—Main branches; an average of 15 cm in length and 4 mm in width, secondary branches; up to 10 cm in length and 3 mm in width, main stem at base; an average of 2 cm in length and 1 cm in width at soil line.

*Stem surface*.—New growth; smooth and glandular, mature stems and bark; smooth and glabrous.

*Stem aspect*.—Held upright to a 45° angle.

*Branching*.—Densely branched; an average of 5 main branches and an average of 4 secondary branches per main branches.

Foliage description:

*Leaf shape*.—Elliptic.

*Leaf division*.—Simple.

*Leaf base*.—Cuneate.

*Leaf apex*.—Rounded to broadly acute.

*Leaf venation*.—Pinnate, not conspicuous, color on upper and lower surface matches leaf coloration with midrib closest to 146C on upper surface and 146D on lower surface.

*Leaf margins*.—Entire.

*Leaf attachment*.—Petiolate.

*Leaf arrangement*.—Alternate.

*Leaf internode length*.—An average of 1 cm and an average of 3 mm in foliage whirl at shoot apex.

*Leaf orientation*.—Held horizontal to an average angle of 45°.

*Leaf aspect*.—Primarily flat.

*Leaf surface*.—Upper and lower surface; smooth, glabrous and finely glandular.

*Leaf color*.—Emerging leaves upper and lower surface; a color between 144B and 138D, mature and fall leaves upper surface; N137A with varying degrees of blending with 202A, mature and fall leaves lower surface; a blend of 146B and 146C, winter leaves upper surface; 200A, winter leaves lower surface; 146C and very slightly diffused with 200D.

*Leaf size*.—Up to 4.5 cm in length and 2.6 cm in width.

*Leaf quantity*.—An average of 11 leaves per branch 15 cm in length.

*Petioles*.—Average of 5 mm in length and 1.5 mm in diameter, 146B in color with lower surface slightly tinged with 166A, smooth, lightly pubescent and glandular surface.

Flower description:

*Inflorescence type*.—Clusters at terminals of main branches and secondary branches.

*Lastingness of flowers*.—An average of 15 days, self-cleaning.

*Inflorescence size*.—Average of 5 cm in height and 8 cm in width (12 flowered cluster).

*Flower size*.—An average of 3 cm in depth and 4.5 cm in diameter.

*Flower fragrance*.—None detected.

*Flower shape*.—Spreading open with base of petals fused into short broad tube.

*Flower number*.—4 to 12 per cluster.

*Flower aspect*.—Upwards to outward.

*Flower bud*.—Elliptic in shape, an average of 2 cm in length and 1 cm in diameter, acute apex, color; a blend of N79B and N79C that blends to 68B near base.

*Flower attachment*.—Pedicellate.

*Petals*.—5, lower ½ fused into tube, elliptic in shape, an average of 3 cm in length and 1.5 cm in width with fused (tube) portion 1.5 cm in height and width, glabrous on upper and lower surfaces and very slightly rugose on upper surface, margins slightly ruffled, apex rounded, color when opening and mature upper and lower surface; a blend of N80B, N80C, 72A and 72B at margins and blending into N80D near base and tube, none fading, throat markings are absent.

*Sepals*.—5, fused into 5 starred calyx, 3.5 mm in diameter and 2 mm in depth with triangular free tips; 1.5 mm in width and 0.5 mm in depth, inner and outer surface glabrous and glandular and 144C in color.

*Pedicels*.—An average of 1.5 cm in length and 1.5 mm in diameter, glandular surface, 144D in color.

*Peduncles*.—None, pedicels are attached directly to the stem in a cluster.

Reproductive organs:

*Gynoecium*.—1 Pistil, stigmas; globular flat disk, 72B in color, 1.5 mm in diameter, style; 2.5 cm in length, slightly curved and 72B to 72C in color, ovary; conical in shape, 3 mm in length and 2 mm in width, 144A in color.

*Androecium*.—10 stamens, anthers; oblong in shape, dorsifixed, and N77A in color, filaments; 2.7 cm in length and 69B in color, pollen; sparse in quantity and 155A in color.

*Fruit/seeds*.—Not observed, it is typical of "PJM" hybrids to exhibit poor seed production.

It is claimed:

1. A new and distinct cultivar of *Rhododendron* plant named 'PJM Elite Star' as herein illustrated and described.

* * * * *